(12) United States Patent
Carter

(10) Patent No.: US 10,172,727 B2
(45) Date of Patent: Jan. 8, 2019

(54) PRE-PROSTHESIS TRAINING DEVICE

(71) Applicant: Daniel Carter, Washington, IL (US)

(72) Inventor: Daniel Carter, Washington, IL (US)

(*) Notice: Subject to any disclaimer, the term of this patent is extended or adjusted under 35 U.S.C. 154(b) by 85 days.

(21) Appl. No.: 15/333,896

(22) Filed: Oct. 25, 2016

(65) Prior Publication Data

US 2017/0112639 A1 Apr. 27, 2017

Related U.S. Application Data

(60) Provisional application No. 62/246,175, filed on Oct. 26, 2015.

(51) Int. Cl.
*A61F 2/76* (2006.01)
*A61F 2/80* (2006.01)
(Continued)

(52) U.S. Cl.
CPC ............... *A61F 2/60* (2013.01); *A61F 2/601* (2013.01); *A61F 2/66* (2013.01); *A61F 2/80* (2013.01);
(Continued)

(58) Field of Classification Search
CPC ...... A61F 2/76; A61F 3/00; A61F 2002/5084; A61F 2002/509; A61F 2002/7605;
(Continued)

(56) References Cited

U.S. PATENT DOCUMENTS 4,161,042 A 7/1979 Cottingham et al.
4,938,775 A 7/1990 Morgan
(Continued)

FOREIGN PATENT DOCUMENTS

| DE | 844 040 | * | 7/1952 | ............... A61F 2/76 |
| FR | 2 669 216 A1 | * | 5/1992 | ............... A61F 2/80 |
| SU | 1018633 A | * | 5/1983 | ............... A61F 2/76 |

OTHER PUBLICATIONS

Computer-generated translation of FR 2 669 216 A1, published in May 1992.*
(Continued)

*Primary Examiner* — David H Willse
(74) *Attorney, Agent, or Firm* — Global Intellectual Property Agency, LLC; Daniel Boudwin

(57) ABSTRACT

A pre-prosthetic training device is provided. The device provides an interim prosthetic device that aids in the standing, weight bearing, and balancing exercises during post-surgery rehabilitation therapy that are required before a prosthesis fitting. The device includes a residual limb support for receiving the residual limb of an amputee, an adjustable pylon for adjusting the height of the residual limb support, and a support base including a plurality of support legs for providing support to the pylon and residual limb support. The residual limb support includes a cushion having a recessed portion sized to receive the distal end of the residual limb of an amputee and for providing comfort and stability thereto. The residual limb support further includes an upper open end and a sidewall including a tapering portion that provides vertical and lateral access, respectively, of a residual limb into the residual limb support.

6 Claims, 3 Drawing Sheets

(51) Int. Cl.
    *A61F 3/00* (2006.01)
    *A61F 2/60* (2006.01)
    *A61F 2/66* (2006.01)
    *G09B 23/30* (2006.01)
    *G06F 19/00* (2018.01)
    *A61F 2/50* (2006.01)
    *A61F 2/78* (2006.01)

(52) U.S. Cl.
    CPC ............. *G06F 19/00* (2013.01); *G09B 23/30* (2013.01); *A61F 2002/502* (2013.01); *A61F 2002/5084* (2013.01); *A61F 2002/607* (2013.01); *A61F 2002/7695* (2013.01); *A61F 2002/785* (2013.01); *A61F 2002/7868* (2013.01); *A61F 2250/0004* (2013.01); *A61F 2250/0007* (2013.01)

(58) Field of Classification Search
    CPC ........ A61F 2002/761; A61F 2002/7695; A61F 2002/7868

USPC ......................................................... 623/28
See application file for complete search history.

(56) References Cited

U.S. PATENT DOCUMENTS 6,368,357 B1    4/2002   Schon et al.
7,303,537 B1   12/2007   Snyder et al.
8,778,031 B1    7/2014   Latour et al.

OTHER PUBLICATIONS

Computer-generated translation of DE 844 040, published in Jul. 1952.*
Computer-generated translation of SU 1018633 A, published in May 1983.*

* cited by examiner

PRE-PROSTHESIS TRAINING DEVICE

CROSS REFERENCE TO RELATED APPLICATIONS

This application claims the benefit of U.S. Provisional Application No. 62/246,175 filed on Oct. 26, 2015. The above identified patent application is herein incorporated by reference in its entirety to provide continuity of disclosure.

BACKGROUND OF THE INVENTION

The present invention relates to therapeutic devices for amputees. More specifically, the present invention relates to a training device for pre-prosthesis amputees that facilitates the transition to a prosthetic limb.

Early fitting of a prosthesis is critical to an amputee's successful rehabilitation. It is very important for the amputee to resume physical activity as soon as possible after amputation for physical, as well as psychological, reasons and because the application of compression to the residual limb is beneficial to the healing process. The early use of a prosthesis helps the amputee quickly re-establish a bilateral body image and accept the use of a prosthetic device. The use of a prosthetic device soon after amputation surgery prevents muscle contractures and loss of muscle strength in the amputee, protects the residual limb from trauma, and helps the amputee develop a tolerance to weight bearing and to learn to balance on a prosthesis. Overall, early use of a post-operative prosthesis reduces complications and the length of the hospital stay for the amputee, and speeds up the training and adjustment period for the new prosthetic device user.

While the residual limb heals after surgery, the amputee cannot be immediately fitted with a permanent prosthesis because of potential wound healing issues, swelling, and the need for dressing. Following surgery, the residual limb undergoes dramatic changes in size and shape. Thus, to accommodate these changes, various preparatory or interim prostheses are employed as a temporary measure for rehabilitation prior to a permanent fitting. For example, before a permanent prosthesis is fitted on an amputee, the amputee must build the strength and endurance required for standing in an upright position without assistance from others. Thus, a comfortable and stable preparatory device that facilitates the standing, weight bearing, and balancing exercises that an amputee must undergo in order to build the adequate strength and endurance needed in order to be fitted for a prosthesis is needed.

It is an object of the present invention to provide a new and improved pre-prosthetic device or interim prosthetic device having a residual limb support having a cushion configured to receive the residual limb of an amputee and an adjustable pylon affixed to a base having supports legs that conjunctively facilitate the standing, weight bearing, and balancing exercises during post-surgery rehabilitation therapy that are required before prosthesis fitting.

SUMMARY OF THE INVENTION

In view of the foregoing disadvantages inherent in the known types of therapeutic devices for amputees now present in the prior art, the present invention provides a pre-prosthesis training device wherein the same can be utilized for providing convenience for the user when undergoing standing, weight bearing, and balancing rehabilitation exercises post amputation surgery and prior to prosthesis fitting.

The present invention comprises a residual limb support including an upper open end, a base, and a sidewall; the base including a cushion comprising a recessed portion configured to receive a distal end of a residual limb of an amputee; wherein the upper open end provides vertical access to the cushion; the sidewall including a horizontal portion and a tapering portion, the horizontal portion including a uniform height and the tapering portion including a tapering height that is less than the height of the horizontal portion; the tapering portion forming an opening in the sidewall providing lateral access to the cushion; a support base including a plurality of support legs disposed on a lower surface thereof, each of the plurality of support legs; an adjustable pylon including a first end and a second end, the first end being affixed to a center of the base of the residual limb support and the second end being affixed to a center of an upper surface of the support base; the adjustable pylon including a plurality of elongated members slidably disposed within one another forming a telescopic arrangement; wherein the adjustable pylon forms a center axis in which the residual limb support and the support base are aligned.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
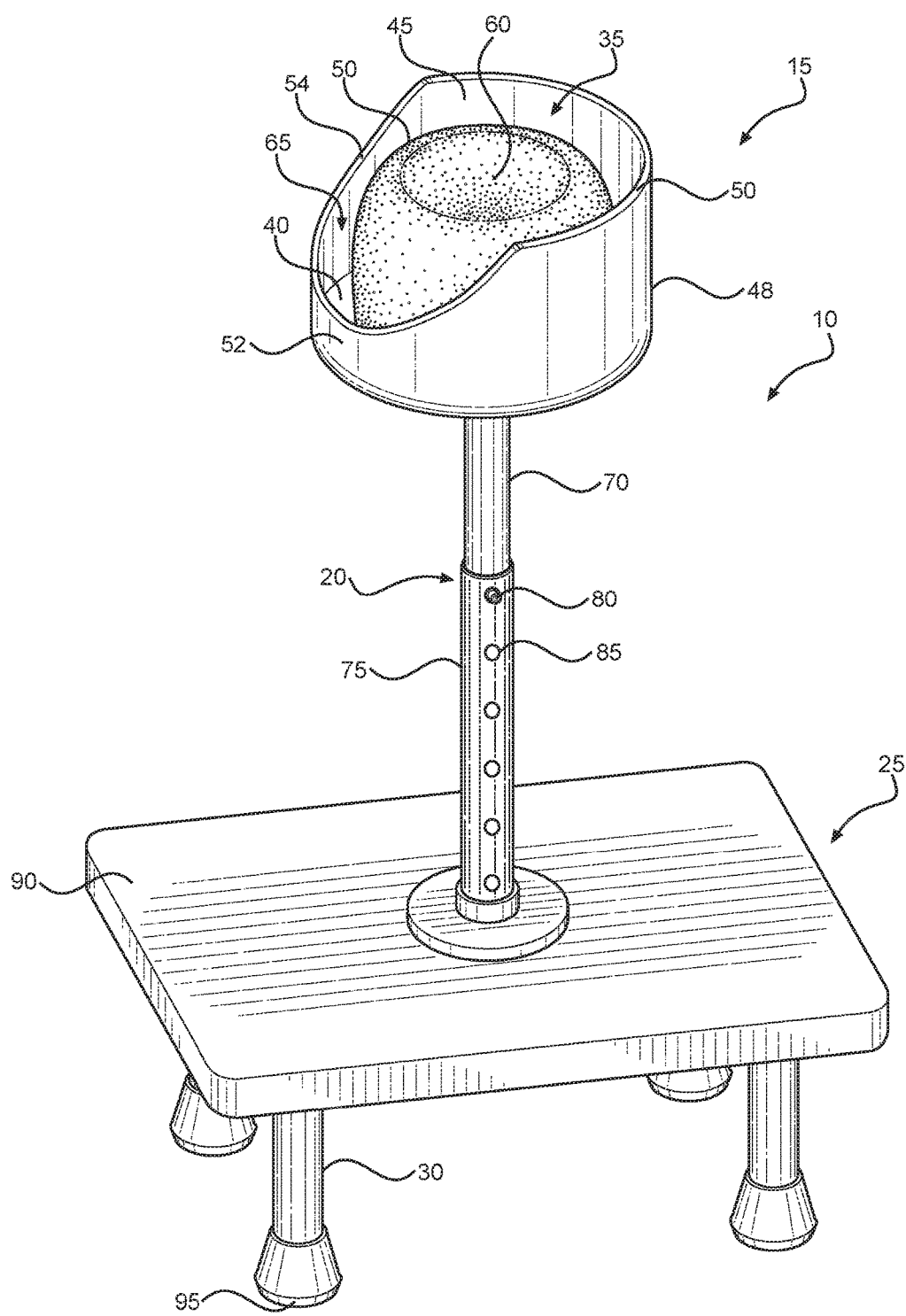
FIG. 1 shows a perspective view of the pre-prosthesis training device.

Reference is made herein to the attached drawings. Like reference numerals are used throughout the drawings to depict like or similar elements of the pre-prosthesis training device. The figures are intended for representative purposes only and should not be considered to be limiting in any respect.

Figure 2:
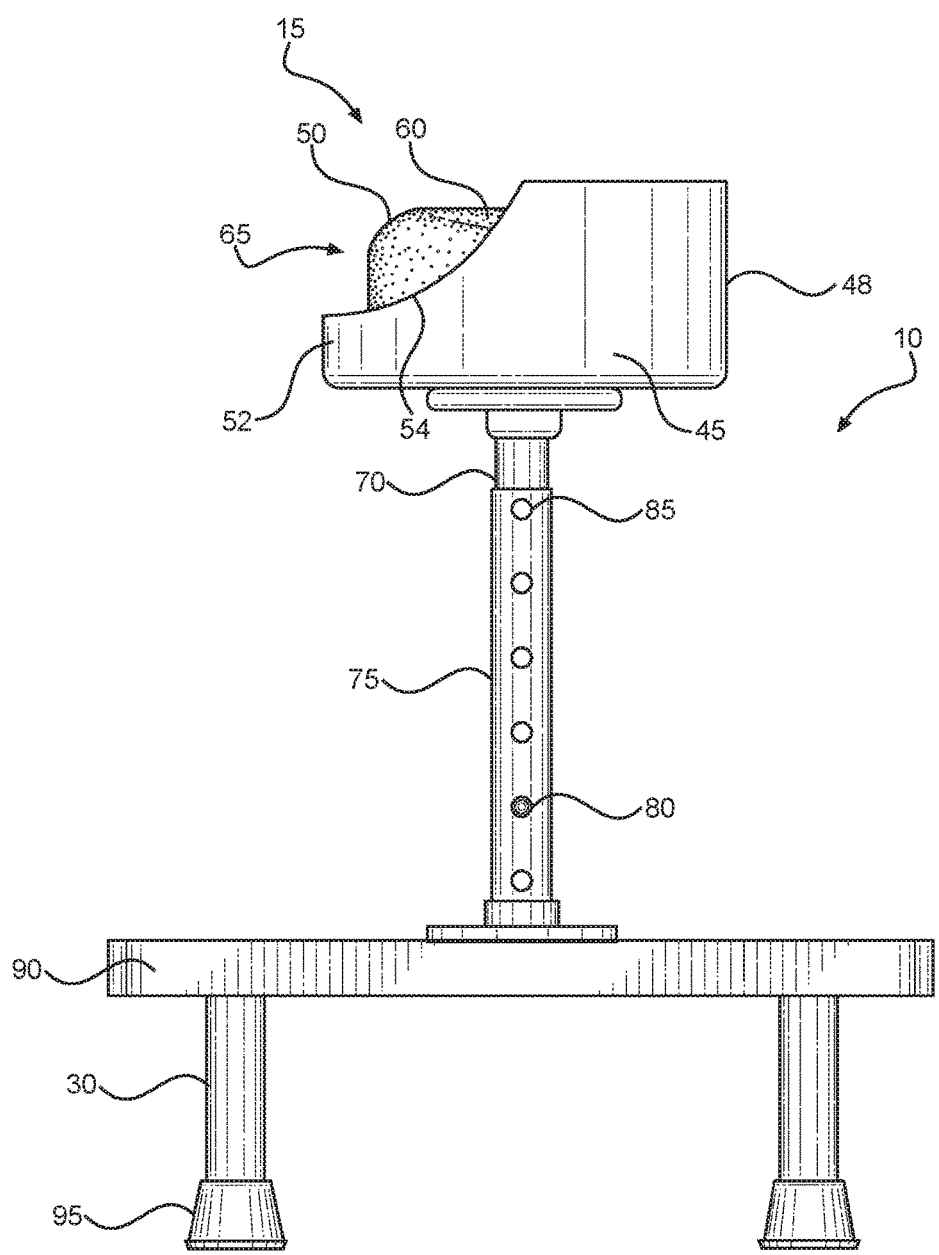
FIG. 2 shows a side view of the pre-prosthesis training device.

Referring now to FIGS. 1 and 2, there is shown a perspective view and a side view of the pre-prosthesis training device, respectively. FIGS. 1 and 2 illustrate a pre-prosthesis training device 10 comprising a residual limb support 15 configured to receive the residual limb of an amputee, an adjustable rod support or pylon 20 for adjusting the height of the residual limb support 15, and a support base 25 including a plurality of support legs 30 for providing support to the residual limb support 15 and pylon 20. The residual limb support 15 is disposed on a first end of the adjustable pylon 20 and the support base 25 is disposed on a second end of the adjustable pylon 20.

The residual limb support 15 comprises an upper open end 35, a base 40, and a sidewall 45 that extends around the base 40 in perpendicular orientation relative to the base 40. In one embodiment, the residual limb support 15 includes a sidewall 45 that extends annularly around the base 40. The base 40 includes a circular cushion 50 that protrudes upwardly from the surface of the base 40. In one embodiment, the cushion 50 is removably attachable to the base 40, such that a user may remove and replace the cushion 50 as desired. In another embodiment, the cushion 50 is integrally affixed to the surface of the base 40 and extends over the entire surface of the base 40 to providing maximum comfort for the residual limb of an amputee. The cushion 50 includes a recessed portion 60 configured to receive the distal end of the residual limb of an amputee and provide further comfort thereto. In one embodiment, the recessed portion 60 is hemispherical in shape for optimizing reception of the stump of the residual limb of an amputee. In alternative embodiments, the recessed portion 60 may be shaped differently and include different depths in order to accommodate differently sized or shaped residual limb distal ends.

The sidewall 45 includes a horizontal portion 48 and a tapering portion 52. The horizontal portion 48 defines a portion of the sidewall 45 that remains uniform in height along a horizontal edge 50, which extends around the sidewall 45 in parallel orientation relative to the base 40. The tapering portion 52 defines a portion of the sidewall 45 that tapers in height along a tapering edge 54, which tapers in height around the sidewall 45 and slopes diagonally at an angle from the horizontal portion 48 towards the base 40. The tapering portion 52 includes a height, at all areas therealong, that is less than the height of the horizontal portion 48. The tapering portion 52 forms a side opening 65 in the sidewall 45 that provides lateral access to the cushion 50, while the open upper end 35 provides vertical access to the cushion 50. The height is defined as the distance between the base 40 and the open upper end 35 of the residual limb support. In the depicted embodiment, the tapering portion 52 comprises a U-shape.

In the illustrated embodiment, the adjustable pylon 20 is defined by a first elongated member 70 slidably disposed in a second elongated member 75, thereby forming an adjustable, telescopic arrangement. The first and second elongated members 70, 75 comprise tubular members; however, in alternative embodiments, the elongated member 70, 75 may comprise rod-like members. In one embodiment, the first and second elongated members 70, 75 are constructed of metal material, such as titanium, steel, aluminum; however, in alternative embodiments, the elongated members 70, 75 may be constructed of carbon fiber or graphite. The first and second elongated members 70, 75 each include a first end and a second end. The first end of the first elongated member 70 is affixed to a center of the base 40 of the residual limb support 15 while the second end of the first elongated member 70 is slidably mounted into the first end of the second elongated member 75. The second end of the second elongated member 75 is affixed to a center of the support base 25.

The first elongated member 70 includes a depressible button 80 that protrudes outwardly and is disposed on its second end. The second elongated member 75 includes a plurality of apertures 85 disposed along its length, wherein the length is defined from the first end to the second end of the second elongated member 75. The plurality of apertures 85 are aligned and sized to receive the button 80 therethrough. The button 80 is biased outwardly such that it can engage each of the apertures 85 and is depressible such that it can be pushed inwardly to disengage each of the apertures 85. In this way, a user can adjust the height of the pylon 20 by depressing the button 80 and releasing it within a desired aperture 85 along the second elongated member 75. The adjustable pylon 20 is vertically disposed between the residual limb support 15 and the support base 25 and defines a center axis of the pre-prosthesis training device 10 in which the residual limb support 15 and the support base 25 are aligned for stability, such that the residual limb support 15 is positioned above the support base 25. In operation, users places the distal end of their residual limb on the cushion 50 and exert a downward force on the pre-prosthesis training device 10, which is aligned such that it is stable when the downward force is applied.

The support base 25 provides support to the residual limb support 15 and the pylon 20. The support base 25 comprises a planar member 90 having an upper surface and a lower surface. The planar member 90 may be constructed of a durable material, such as plastic, wood, or metal. The second elongated member 75 of the pylon 20 is affixed to a center of the upper surface of the planar member 90 and the plurality of support legs 30 are disposed on the lower surface of the planar member 90. In one embodiment, the support base 25 includes a rectangular shaped cross section and comprises four support legs 30 positioned adjacent to each corner of the lower surface of the support base 25. The support legs 30 extend downwardly and perpendicularly relative to the planar member 90. The support legs 30 each comprise a tubular member; however, in alternative embodiments, the support legs 30 may comprise rectangular or rod-like members. Each of the support legs 30 includes a grip 95 at an end thereof that is adapted to engage the ground to prevent slippage. In one embodiment, the grip 95 is a rubber grip.

Figure 3:
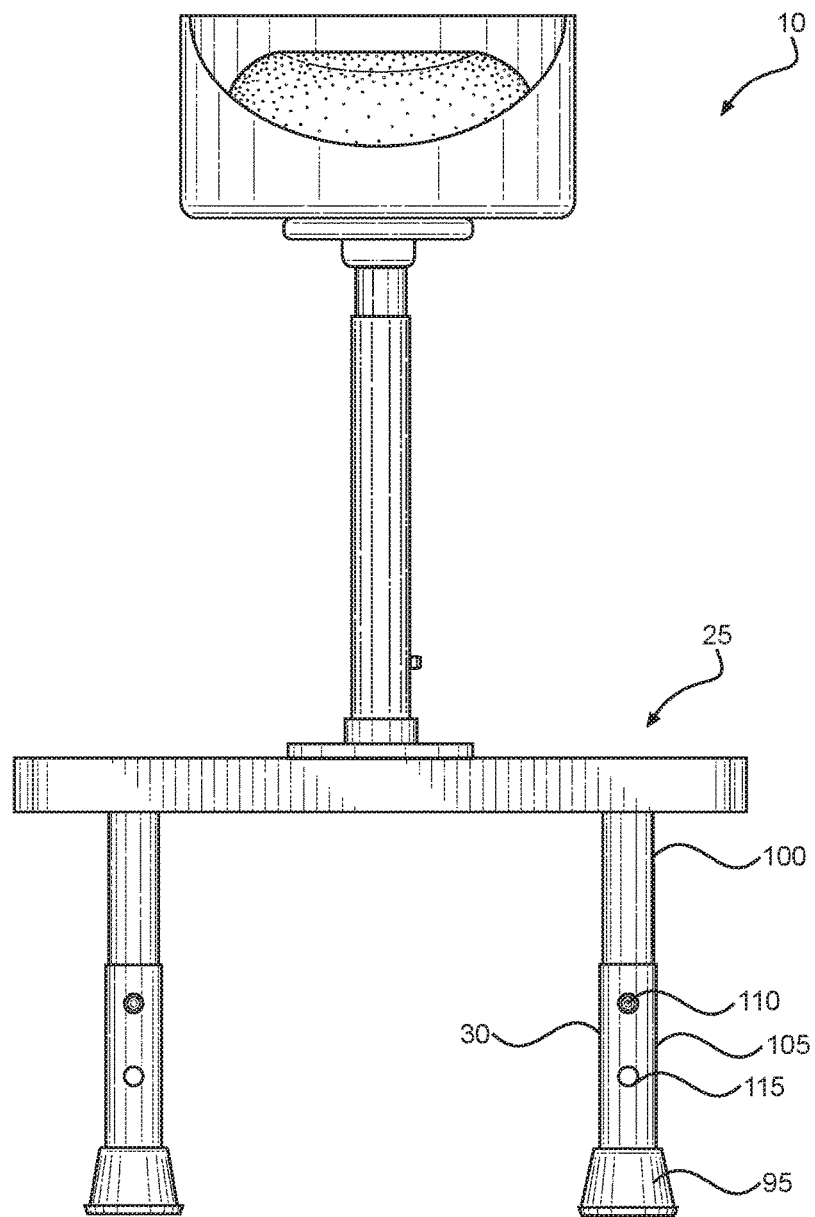
FIG. 3 shows a front view of the pre-prosthesis training device.

Referring now to FIG. 3, there is shown a front view of the pre-prosthesis training device. In one embodiment of the pre-prosthesis training device 10, each of the plurality of supports legs 30 comprises a first member 100 slidably disposed in a second member 105, thereby forming an adjustable, telescopic arrangement. The first and second members 100, 105 each include a first end and a second end. The first end of the first member 100 is affixed to the lower surface of the support base 25 while the second end of the first member 100 is slidably mounted into the first end of the second member 105. The second end of the second member 105 includes the grip 95.

The telescopic support legs 30 can be locked in position by an adjustment mechanism, wherein the adjustment mechanism includes a depressible button 110 disposed on the second end of the first member 100 and a plurality of apertures 115 vertically aligned along the linear length of the second member 105. The button 110 is biased outwardly such that it can engage the plurality of apertures 115 and depressible such that it can be pushed inwardly to disengage the plurality of apertures 115. In this way, a user can adjust the height of each of the legs 30 by depressing the button 110 and releasing it within a desired aperture along the second member 105.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A pre-prosthesis training device for the residual limb of an amputee, comprising:
    a residual limb support including an upper open end, a base, and a sidewall;
    the base including a cushion comprising a recessed portion configured to receive a distal end of a residual limb of an amputee;
    wherein the upper open end provides vertical access to the cushion;
    the sidewall including a horizontal portion and a tapering portion, the horizontal portion including a uniform height and the tapering portion including a tapering height that is less than the height of the horizontal portion;
    the tapering portion forming an opening in the sidewall providing lateral access to the cushion;
    a support base including a plurality of support legs disposed on a lower surface thereof, each of the plurality of support legs;
    an adjustable pylon including a first end and a second end, the first end being affixed to a center of the base of the residual limb support and the second end being affixed to a center of an upper surface of the support base;
    the adjustable pylon including a plurality of elongated members slidably disposed within one another forming a telescopic arrangement;
    wherein the adjustable pylon forms a center axis in which the residual limb support and the support base are aligned.

2. The pre-prosthesis training device of claim 1, wherein the recessed portion is hemispherical in shape.

3. The pre-prosthesis training device of claim 1, wherein the plurality of elongated members of the adjustable pylon comprise a first elongated member and a second elongated member, the first and second elongated members each including a first end and a second end;
    the first end of the first elongated member being affixed to a center of the base of the residual limb support and the second end of the first elongated member being slidably mounted into the first end of the second elongated member; and
    the second end of the second elongated member being affixed to a center of the support base.

4. The pre-prosthesis training device of claim 3, wherein the first end of the first elongated member includes a depressible button protruding outwardly therefrom and the second elongated member includes a plurality of apertures vertically aligned along a linear length thereof;
    wherein the depressible button is configured to slidably engage the plurality of apertures.

5. The pre-prosthesis training device of claim 1, wherein each of the plurality of support legs comprises a first member and a second member, the first and second members each including a first end and a second end;
    the first end of the first member being affixed to the lower surface of the support base;
    the second end of the first member being slidably mounted into the first end of the second member;
    the second end of the second member including a grip.

6. The pre-prosthesis training device of claim 5, wherein each of the plurality of supports legs further includes an adjustment mechanism for adjusting the height of the support legs relative to the ground, the adjustment mechanism comprising;
    a depressible button disposed on the second end of the first member; and
    a plurality of apertures vertically aligned along a linear length of the second member;
    wherein the depressible button is configured to slidably engage the plurality of apertures.

\* \* \* \* \*